United States Patent [19]

Dixon et al.

[11] Patent Number: 4,647,663

[45] Date of Patent: Mar. 3, 1987

[54] SYNTHESIS OF MORPHOLINE

[75] Inventors: Dale D. Dixon, Kutztown, Pa.; Randall J. Daughenbaugh, Longmont, Colo.

[73] Assignee: Air Products and Chemicals, Inc., Allentown, Pa.

[21] Appl. No.: 381,993

[22] Filed: May 25, 1982

[51] Int. Cl.$^4$ ............................................ C07D 295/02
[52] U.S. Cl. ..................................................... 544/106
[58] Field of Search ........................................ 544/106

[56] References Cited

U.S. PATENT DOCUMENTS

| | | | |
|---|---|---|---|
| 2,412,209 | 12/1946 | Dickey et al. | 564/480 |
| 2,529,923 | 11/1950 | Dickey et al. | 544/106 |
| 3,151,112 | 9/1964 | Moss | 544/106 |
| 3,151,113 | 9/1964 | Advani et al. | 544/106 |
| 3,154,544 | 10/1964 | Langdon et al. | 544/106 |
| 3,155,657 | 11/1964 | Bedoit, Jr. | 544/106 |
| 4,091,218 | 5/1978 | Advani | 544/106 |

FOREIGN PATENT DOCUMENTS 4439936  9/1971  Japan .
1394030  5/1975  United Kingdom .
1530570  11/1978  United Kingdom .

OTHER PUBLICATIONS

Satterfield, *A.I.Ch.E. Journal*, vol. 21 (1975) pp. 209, 210.
Ross, *Chemical Eng. Progress*, vol. 61 (1965) pp. 77, 78.

*Primary Examiner*—Robert W. Ramsuer
*Attorney, Agent, or Firm*—Russell L. Brewer; E. Eugene Innis; James C. Simmons

[57] ABSTRACT

This invention relates to an improved process for producing morpholine. The improvement resides in continuously charging the diethylene glycol and ammonia to a first trickle bed reactor, operating the reactor under conditions such that the diethylene glycol is maintained as a discontinuous liquid phase and the morpholine formed is predominantly in the vapor phase, separating the reaction products into a morpholine stream and a 2-(2,aminoethoxy)ethanol stream, and then charging the 2-(2,aminoethoxy)ethanol stream to a second trickle bed reactor and then reacting with ammonia to produce morpholine.

10 Claims, No Drawings

SYNTHESIS OF MORPHOLINE

DESCRIPTION OF THE PRIOR ART

Heretofore, the general method for producing morpholine has been to react diethylene glycol or 2-(2 aminoethoxy)ethanol with ammonia. Representative patents showing this technique are:

U.S. Pat. No. 2,412,209 discloses a process for producing aliphatic amines from alcohols and particularly morpholine by the reaction of diethylene glycol and ammonia. Temperatures from 160°–400° C. are used and the reaction is carried out in the presence of a hydrogenation catalyst. Examples of hydrogenation catalysts suited for the reaction include Raney nickel, copper chromite, copper-nickel-chromite, iron, cobalt, etc. Liquid or gas phase conditions are suggested.

U.S. Pat. No. 3,154,544 discloses the preparation of substituted morpholines by the vapor phase conversion of a dialkylene glycol having at least one secondary hydroxyl group with hydrogen, and ammonia, in the presence of a hydrogenation/dehydrogenation catalyst. It is noted in the reference that diethylene glycol could not be converted to morpholine by reaction with ammonia in substantial conversion or yield, particularly under conditions suggested in the prior art e.g. U.S. Pat. Nos. 2,412,209 or 2,529,923.

Others include U.S. Pat. Nos. 3,155,657; 3,151,112, 3,151,113, Japanese publication No. 46-32188 and U.S. Pat. No. 4,091,218.

More recently, it has been shown that 2,-(2-aminoethoxy)ethanol can be reacted with ammonia to produce morpholine in high yields. Representative patents showing these processes are:

British Pat. No. 1,530,570 discloses a process for producing (2-aminoalkoxy)alkanol (AEE) and morpholine derivatives from ammonia and oxydialkanol under pressures sufficient to maintain liquid conditions. Temperature and pressure are controlled in order to vary the quantity of the aminoethoxyethanol and morpholine derivative produced. Temperatures generally are 200°–220° C. while gauge pressures of at least 700 psig are used. Ammonia to alkanol ratios of 6:1 are used, with the ammonia being in the anhydrous form. Hydrogen is added to maintain catalyst activity.

British Pat. No. 1,394,030 discloses reacting 2,-(2-aminoethoxy)ethanol with ammonia over a hydrogenation dehydrogenation catalyst at a temperature of 150°–400° C. at a pressure from 20–400 atmospheres. The reaction is characterized as producing no by-product ethylene glycol monomethyl ether.

SUMMARY OF THE INVENTION

This invention relates to an improved process for forming morpholine from diethylene glycol. The basic process comprises reacting a dialkylene glycol and ammonia in the presence of hydrogen and a hydrogenation/dehydrogenation catalyst at conventional temperatures. The basic process is shown in U.S. Ser. No. 130,782, having a filing date of Mar. 17, 1980 now abandoned, and is incorporated by reference. The improvement constituting the basis of this invention resides in (a) charging the reactants downflow through a first trickle-bed catalytic reactor;

(b) operating the reactor under conditions such that at least a portion of the diethylene glycol is present as a discontinuous liquid phase;

(c) removing reaction product containing morpholine, 2,-(2-aminoethoxy)ethanol, unreacted by-products and contaminants from the trickle bed reactor;

(d) separating the reaction product into a morpholine stream and a 2,-(2-aminoethoxy)ethanol stream; and (e) charging the 2,-2(aminoethoxy)ethanol stream downflow through a second trickle bed reactor and reacting with ammonia in the presence of hydrogen, said reaction operated at a temperature from 140° to 280° C. and a pressure of from 125 to 500 psig.

Another embodiment involves an improved process for producing morpholine from 2-(2-aminoethoxy)ethanol.

Several advantages are associated with the improved process of this invention as compared to the prior art. These include:

the reaction permits substantially complete conversion of the 2,(2-aminoethoxy)ethanol to morpholine, thereby minimizing recovery problems and minimizing recycle;

the reaction conditions are moderate e.g. low pressures are used thereby resulting in an energy saving as compared to prior art processes operating under high pressure, liquid phase conditions; and high selectivity to morpholine with little formation of heavies in the form of polyamines, e.g. morpholino diethylene glycol (MDEG) and bis-morpholino diethylene glycol (BMDEG) or ethers.

DESCRIPTION OF THE PREFERRED EMBODIMENTS

In the process of the invention one of the feed components for reaction with ammonia is 2,(2-aminoethoxy)-ethanol (AEE) and is represented by the formula:

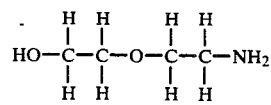

While the process does not require ammonia to permit reaction on a stoichiometric basis, ammonia is added to maintain catalyst activity. The preferred $NH_3/AEE$ mole ratio is 4 to 16:1 molar ratios higher than about 16 to 20:1 do not result in significant advantages. Because of the unique nature of the reaction conditions for carrying out the process, higher ratios of ammonia to AEE can have a detrimental effect in commercial units in that such higher ratios may require increased pressures.

In the morpholine processes hydrogen is necessary for the proper and efficient conduct of the process. It is used in combination with ammonia and it is believed its function is to maintain catalyst activity. Molar ratios of ammonia to hydrogen used in the process generally are from about 4 to 60:1 and preferably about 6 to 32:1. Low ratios of ammonia to hydrogen, e.g. 2:1 to about 4:1 generally result in increased heavies formation. It is believed lower ammonia to hydrogen ratios reduce the ammonia content in the liquid phase thereby permitting any residual liquid phase morpholine to react and form heavies. Such is also true with the introduction of other inert gases such as nitrogen or methane. They, like hydrogen, reduce the ammonia content in the liquid phase and which results in increased heavy formation.

The hydrogenation/dehydrogenation catalysts suited for practicing the invention include those commonly used in prior art morpholine processes provided that they are wettable with the diethylene glycol or AEE under the reaction conditions. By wettable, it is meant the catalyst will permit the formation of a very thin, liquid film about the surface of the catalyst as required in a trickle bed. The hydrogenation/dehydrogenation catalysts suited for practicing the process generally includes one or more metals from the group consisting of copper, nickel, cobalt, chromium, molybdenum, manganese, platinum, palladium, ruthenium, and rhodium. The preferred catalysts i.e. those which are most effective for the reaction are nickel, cobalt, and copper or contain such components.

Most of the above hydrogenation/dehydrogenation metals, even in highly porous form, will not permit the formation of a thin film of diethylene glycol or AEE about its surface, but rather will cause it to bead up on the surface. In those cases, the metal should be impregnated or incorporated into a wettable support. The support for the hydrogenation/dehydrogenation catalyst then is (a) one which is inert to the extent that it is not soluble or reactable with the reaction medium and (b) one which is wettable by the diethylene glycol or AEE. Supports suited include silica, alumina, kieselguhr, and others conventionally used in the art. Alumina and silica are preferred. Broadly, the proportion of hydrogenation/dehydrogenation metal by weight of the catalyst, including support, is from about 0.01% to 70% and typically between 20 to 40%. This level may vary to the extent the catalyst loses its wettability.

In practicing the process, the temperature and pressure are maintained in the catalytic reaction zone such that some, at least about 1% preferably at least 5%, by weight of the reactant DEG in the first trickle-bed reactor or 1-5% by weight of the AEE in the other reactor is in the liquid phase, while the morpholine product is predominantely in the vapor phase, e.g. greater than 80 mole % and preferably 90%, assuming 90% conversion of the AEE. In addition, the temperature and pressure are selected so the reaction conditions do not substantially exceed (greater than about 10° C.) the dew point temperature of the feed. Techniques for calculating the necessary conditions are noted in U.S. Ser. No. 130,782.

In a preferred mode for carrying out the process, i.e., that of maintaining some of the AEE in the liquid phase with the predominant portion of the morpholine in the vapor phase, the reactants are fed downflow through a trickle-bed reactor. In this way, the diethylene glycol in the first reactor or AEE in the other reactor (if DEG is used as the starting material) is present as a discontinuous liquid phase. This inhibits flooding of the bed and hold up of gaseous product. Using this technique, the conversion of AEE to morpholine is high and the percentage of heavies in the form of polyamines (MDEG and BMDEG) is low. (The production of by-product ethylene glycol monoethyl ether is not a problem in trickle-bed operation.)

To permit the maintenance of an appropriate contact time in the reaction zone for the conversion of AEE to morpholine, the reaction is generally carried out at a liquid hourly space velocity of from 0.05 to 2.5 hr.$^{-1}$. (Liquid hourly space velocity (LHSV) is defined as the ratio of the volume of liquid AEE per volume of catalyst per hour.) The liquid hourly space velocity is not as critical as some other parameters in the process in that it is largely dependent upon the activity of the catalyst. In those instances where the catalyst is highly reactive, a higher liquid hourly space velocity can be utilized to achieve greater throughput. Alternatively, where a catalyst having lower activity is used, lower space velocities are employed. Generally, liquid hourly space velocity is adjusted to permit the greatest conversion based on desired throughput. Commercially, it is possible to operate at a lower conversion and obtain greater product yield in view of the increased throughput through the reactor. Of course this will result in increasing the amount of by-product material coming from the reactor that must be recycled or recovered. A preferred LHSV range for cobalt or nickel containing catalysts is from about 0.2 to 1.0 hr.$^{-1}$.

The pressure used for the reaction is adjusted to meet desired vapor-liquid criteria for the reactants and products, i.e. a condition where the diethylene glycol or AEE is predominantely in the liquid phase and the morpholine is in the vapor phase. These conditions can be determined from known vapor-liquid data. In addition, the pressure must be adjusted to provide for a desired rate of reaction. Pressures generally suited for commercial operation, whether using diethylene glycol in one reactor and AEE in another, are from 125 to 500 psig. However, pressures generally higher than 300 psig generally are not used as they show no significant improvement in the trickle bed reactor. Pressures above about 500 psig can result in increased heavies formation. Preferred pressures are about 200-300 psig.

The temperature used for carrying out the reaction generally is from about 140° to 280° C. at the pressure specified. Of course as the pressure is increased, temperatures can be increased to the extent the vapor-liquid equilibrium criteria is met. Typically, the temperature used is from 200° to 250° C. Higher temperatures often cause coking of the catalyst or deactivation.

The following examples are representative of the preferred embodiments of the invention.

EXAMPLE 1

Initially in runs 1-9 diethylene glycol feedstocks were converted to morpholine in a process design unit reactor which consisted of 0.41 inch (I.D.) 304 stainless steel tubing encased in aluminum block. The reactor was Model R-100 designed by the Ace Catalyst Company. The reactor utilized electrical heat for temperature control. Ten cc of catalyst to provide a reaction zone bed depth of about 10 centimeters were charged to the reactor. A catalyst containing 42% nickel oxide carried on a gamma alumina support had been crushed and sized to 12-18 mesh and the nickel oxide reduced at 750° F. with hydrogen. The surface area was approximately 190 m$^2$ per gram and was supplied under the trademark HSC-102B by the Houdry Division of Air Products and Chemicals, Inc.

In the process the reactor was operated as a trickle bed reactor at a variable LHSV, based on diethylene glycol, and variable hydrogen, diethylene glycol, and ammonia molar feed ratios. Hydrogen feed rates were measured in ml/min. at STP whereas ammonia and DEG were measured in ml/hr. Product distribution is given in gas chromatograph area percent.

The feed DEG, including NH$_3$ and H$_2$ was passed downflow through the reactor at various temperatures ranging from 190°-260° C. The liquid DEG was present in the reactor as a discontinuous phase. Conversion results are shown in Table I. DEG represents diethylene glycol, MOR represents morpholine and AEE represents 2-(2-aminoethoxy)ethanol. The liquid-vapor equilibrium values were calculated assuming 90% diethylene glycol conversion and 71% AEE conversion.

TABLE 1

| Run | Temp. °C. | (psig) Press. | ml/min STP H$_2$ | ml/hr DEG | ml/hr NH$_3$ | H$_2$/DEG/NH$_3$ Mole Ratio | (DEG) LHSV | MOR | AEE | DEG | MDEG | Others |
|---|---|---|---|---|---|---|---|---|---|---|---|---|
| 1 | 240 | 250 | 15 | 7.5 | 18 | 0.5/1/8 | 0.5 | 32 | 31 | 29 | 3.5 | 4.4 |
| 2 | 250 | 250 | 15 | 7.5 | 18 | " | 0.5 | 37 | 23 | 30 | 1.3 | 8.3 |
| 3 | 190 | 280 | 44 | 3.8 | 6.8 | 3/1/6 | 0.25 | 31 | 21 | 30 | 14 | 3.7 |
| 4 | 210 | 140 | 44 | 3.8 | 6.8 | " | 0.25 | 26 | 19 | 35 | 15 | 4.2 |
| 5 | 210 | 280 | 44 | 3.8 | 6.8 | " | 0.25 | 29 | 19 | 31 | 17 | 4.1 |
| 6 | 210 | 280 | 7.5 | 3.8 | 9.8 | 0.5/1/8.5 | 0.25 | 26.2 | 32 | 37 | 3.7 | 1.2 |
| 7 | 209 | 700 | — | — | — | 0.9/1/6.4$^V$ | 0.61 | 49 | 18 | 15 | 16 | 2.3 |
| 8 | 210 | 1400 | — | — | — | 0.9/1/6.34$^V$ | 0.59 | 45 | 20 | 26 | 7.0 | 2.1 |
| 9 | 210 | 2625 | — | — | — | 0.9/1/5.97$^V$ | 0.61 | 28 | 17 | 50 | 3.5 | 1.9 |

$^V$Reactor feed also includes 6.6 moles H$_2$O/mole DEG and 0.3 moles N$_2$/mole DEG.

EXAMPLE 2

The procedure for Runs 1-9 in Example 1 was followed except that 20 cc (33.14 gm) of a copper chromite catalyst were used in place of the nickel catalyst and 2-(2-aminoethoxy)ethanol was used as the feed. The specific catalyst used was Harshaw Cu 0203 contains 78% CuO; 20% Cr$_2$O$_3$. It was activated by heating to 132° C. under N$_2$ followed by heating in the presence of H$_2$ much like the nickel catalyst in Example 1. Once under the hydrogen flow, the temperature was increased to 300° C. (The copper chromite catalyst was not as successful as the nickel catalyst using diethylene glycol as the feed in Example I, presumably because of contamination by the heavies but it was more effective than nickel in the reaction of 2-(2 aminoethoxy)ethanol. Otherwise, the comparison would have been made with the copper catalyst.

The conditions and results are listed in Table 2.

TABLE 2

| Run | Temp. °C. | (psig) Press. | ml/min STP H$_2$ | ml/hr AEE | ml/hr NH$_3$ | Mole Ratio H$_2$/AEE/NH$_3$ | DEG | AEE | Morpholine | Heavies | Unidentified Lights |
|---|---|---|---|---|---|---|---|---|---|---|---|
| 1 | 200 | 250 | 20 | 9.5 | 9.5 | 0.05/1/3.5 | 0.3 | 36.13 | 59.5 | 0 | 4.06 |
| 2 | 220 | 250 | 20 | 9.5 | 9.5 | 0.05/1/3.5 | 1.29 | 2.37 | 90.8 | 0 | 5.5 |
| 3 | 200 | 250 | 20 | 11 | 38 | 0.05/1/12 | 0.02 | 53.7 | 39.2 | 3.77 | 3.24 |
| 4 | 220 | 250 | 20 | 11 | 38 | 0.05/1/12 | 0.29 | 25.9 | 67.2 | 0 | 6.4 |
| 5 | 240 | 250 | 20 | 11 | 38 | 0.05/1/12 | 0.5 | 20.6 | 63.3 | 0 | 7.5 |
| 6 | 220 | 250 | 20 | 9.5 | 9.5 | 0.05/1/3.5 | 0.23 | 0.7 | 95.4 | 0 | 3.7 |

The results in Table 2 show that good conversion of AEE to morpholine can be accomplished with almost no heavies formation. Although heavies formation was low in the Example 1 processes, the results in Table 2 show that conversion can be enhanced and selectivity increased by separating the AEE from the reaction mixture of DEG and NH$_3$ in morpholine production and using AEE as to feed.

STATEMENT OF INDUSTRIAL APPLICATION

This process is capable of manufacturing morpholine with high conversion of reactant and good selectivity. Morpholine is an industrial chemical useful as a corrosion inhibitor and also suited for manufacturing a variety of materials e.g. herbicides.

What we claim is:

1. In a process for producing morpholine by the reaction of diethylene glycol and ammonia in a reactor, said reaction being carried out in the presence of hydrogen and a hydrogenation-dehydrogenation catalyst, the improvement which comprises:

(a) continuously charging the diethylene glycol and ammonia to a first trickle bed reactor;
   (b) operating the reactor under conditions such that at least 1% of the diethylene glycol is maintained as a discontinuous liquid phase and any morpholine formed during the reaction is predominately in the vapor phase;
   (c) continuously removing reaction product containing morpholine, 2-(2,aminoethoxy)ethanol, unreacted by-products and contaminants from the trickle bed reactor;
   (d) separating the reaction products into a morpholine stream and a 2-(2,aminoethoxy)ethanol stream;
   (e) charging the 2-(2,aminoethoxy)ethanol to second trickle bed reactor;
   (f) operating the second trickle bed reactor under conditions such that at least a portion of the 2-(2,aminoethoxy)ethanol is maintained as a discontinuous liquid phase; and
   (g) reacting with ammonia in the presence of hydrogen, said reactor operated at a temperature of from 140° to 280° C. and a pressure of from 125 to 500 psig. and said reactor operated under conditions such that any morpholine formed during the reaction is predominately in the vapor phase.

2. The process of claim 1 wherein the temperature maintained in the first and second trickle bed reactor is from about 200° to 250° C.

3. The process of claim 2 wherein the pressure maintained in the first and second trickle bed reactor is from about 200 to 300 psig.

4. The process of claim 3 wherein the liquid hourly space velocity, based on diethylene glycol feed in the first trickle bed reactor is from about to 0.05 to 2.5, and the liquid hourly space velocity based upon 2-(2,aminoethoxy)ethanol in the second trickle-bed reactor is from 0.05 to 2.5.

5. The process of claim 4 wherein the hydrogenation-dehydrogenation catalyst in the first and second trickle bed reactor is wettable by the diethylene glycol or AEE and is carried on a support selected from the group consisting of alumina, silica, and mixtures thereof.

6. The process of claim 5 wherein said hydrogenation-dehydrogenation catalyst carried upon the support contains a component selected from the group consisting of nickel, cobalt and chromium.

7. In a process for producing morpholine by reacting 2-(2,aminoethoxy)ethanol with ammonia in the presence of hydrogen over a hydrogenation catalyst, the improvement for reducing heavies formation which comprises:
    (a) charging the 2-(2,aminoethoxy)ethanol downflow through a trickle-bed reactor; and
    (b) operating the reactor under conditions such that at least a portion of the 2-(2,aminoethoxy)ethanol is maintained as a discontinuous phase, said reactor being operated at a temperature from 140°–280° C. and a pressure of from 125 to 500 psig and said reactor operated under conditions such that any morpholine formed during the reaction is predominately in the vapor phase.

8. The process of claim 7 wherein said temperature is from 200°–250° C., said pressure is from 200 to 300 psig, and said charging is at a rate to provide an LHSV based on said 2-(2,aminoethoxy)ethanol of 0.05–2.5.

9. The process of claim 7 wherein said catalyst in said reactor is a copper-chromite containing catalyst.

10. The process of claim 8 wherein the molar ratio of ammonia to 2-(2,aminoethoxy)ethanol in the reactors is from 4–16:1.

* * * * *